US010229068B2

(12) United States Patent
Wagh et al.

(10) Patent No.: US 10,229,068 B2
(45) Date of Patent: Mar. 12, 2019

(54) TUNABLE OBLIVIOUS RAM

(71) Applicants: Sameer Wagh, Princeton, NJ (US);
Paul Cuff, Lawrenceville, NJ (US);
Prateek Mittal, Princeton, NJ (US)

(72) Inventors: Sameer Wagh, Princeton, NJ (US);
Paul Cuff, Lawrenceville, NJ (US);
Prateek Mittal, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 244 days.

(21) Appl. No.: 15/393,822

(22) Filed: Dec. 29, 2016

(65) Prior Publication Data

US 2017/0185534 A1    Jun. 29, 2017

Related U.S. Application Data

(60) Provisional application No. 62/272,499, filed on Dec. 29, 2015.

(51) Int. Cl.
*G06F 12/14* (2006.01)
*G06F 21/62* (2013.01)
*G06F 21/00* (2013.01)

(52) U.S. Cl.
CPC .......... *G06F 12/1408* (2013.01); *G06F 21/00* (2013.01); *G06F 21/6245* (2013.01); *G06F 2212/402* (2013.01)

(58) Field of Classification Search
None
See application file for complete search history.

(56) References Cited

U.S. PATENT DOCUMENTS

| 9,055,038 B1* | 6/2015 | Lu ..................... H04L 63/0428 |
| 2014/0007250 A1* | 1/2014 | Stefanov ................ G06F 21/60 726/26 |
| 2016/0019211 A1* | 1/2016 | Patey ..................... H04L 9/00 707/747 |
| 2016/0070918 A1* | 3/2016 | Ciordas .................. G06F 21/14 726/27 |

OTHER PUBLICATIONS

Dautrich Jr, Jonathan L., et al., "Compromising privacy in precise query protocols," In Proceedings of the 16th International Conference on Extending Database Technology, 2013, pp. 155-166, ACM, California.

(Continued)

*Primary Examiner* — Michael Alsip
(74) *Attorney, Agent, or Firm* — Occhiuti & Rohlicek LLP

(57) ABSTRACT

An approach to implementing or configuring an Oblivious RAM (ORAM), which in addition to behaving as a RAM, provides a way to meet a specified degree of privacy in a manner that avoids applying unnecessary computation resources (computation time and/or storages space and/or data transfer) to achieve the specified degree of privacy. In this way, a tradeoff between privacy and computation resources may be tuned to address requirements of a particular application. This ability to tune this tradeoff is not found in other ORAM implementations, which in general aim to achieve complete privacy. In some implementations, the ORAM provides a constant bandwidth overhead compared to conventional RAMs, while achieving a statistical privacy as desired by the user.

15 Claims, 3 Drawing Sheets

(56) References Cited

OTHER PUBLICATIONS

Dwork, Cynthia, et al., "Our data, ourselves: Privacy via distributed noise generation," In Annual International Conference on the Theory and Applications of Cryptographic Techniques, 2006, pp. 486-503, Springer Berlin Heidelberg, California.
Dautrich, Jonathan, et al., "Burst ORAM: Minimizing ORAM response times for bursty access patterns," In 23rd USENIX Security Symposium (USENIX Security 14), 2014, pp. 749-764, 17 pages, San Diego.
Dwork, Cynthia, "Differential privacy," Automata, languages and programming, ICALP 2006, Part II, LNCS 4052, pp. 1-12.
Gentry, Craig, et al., "Optimizing ORAM and using it efficiently for secure computation," In International Symposium on Privacy Enhancing Technologies Symposium, 2013, pp. 1-18, Springer Berlin Heidelberg.
Goldreich, Oded et al., "Software protection and simulation on oblivious RAMs," Journal of the ACM (JACM) 43, No. 3, 1996, pp. 431-473, 43 pages.
Islam, Mohammad Saiful, et al., "Access Pattern disclosure on Searchable Encryption: Ramification, Attack and Mitigation," In NDSS, vol. 20, p. 12, 2012, 15 pages.
Ren, Ling et al., "Constants count: Practical improvements to oblivious RAM," In 24th USENIX Security Symposium (USENIX Security 15), 2015, pp. 415-430, 17 pages.
Ren, Ling et al., "Ring ORAM: Closing the Gap Between Small and Large Client Storage Oblivious RAM," IACR Cryptology ePrint Archive Report 2014/431, 2014, 16 pages.
Stefanov, Emil et al., "Oblivistore: High performance oblivious cloud storage," 2013 IEEE Symposium on Security and Privacy, pp. 253-267.
Stefanov, Emil et al., "Towards practical oblivious RAM," arXiv preprint arXiv:1106.3652, 2011, 15 pages.
Stefanov, Emil et al., "Path ORAM: an extremely simple oblivious RAM protocol," In Proceedings of the 2013 ACM SIGSAC conference on Computer & communications security, 2013, pp. 299-310, ACM.
Goldreich, Oded, "Towards a Theory of Software Protection and Simulation by Oblivious RAMs," ACM, 1987, pp. 182-194.

\* cited by examiner

TUNABLE OBLIVIOUS RAM

CROSS-REFERENCE TO RELATED APPLICATIONS

This application claims the benefit of U.S. Provisional Application No. 62/272,499, filed Dec. 29, 2015, which is incorporated by reference.

FEDERAL SPONSORSHIP

This invention was made with government support under Grant No. CCF-1350595 and Grant No. CNS-1409415 awarded by the National Science Foundation and Grant No. FA9550-15-1-0180 awarded by the U.S. Air Force Office of Scientific Research. The government has certain rights in the invention

PRIOR DISCLOSURES BY INVENTOR

Sameer Wagh, Paul Cuff, Prateek Mittal, "Root ORAM: A Tunable Differentially Private Oblivious RAM," Jan. 13, 2016. http://arxiv.org/abs/1601.03378v1

BACKGROUND

This application relates to Oblivious Random Access Memory (ORAM), and more particularly relates to an approach in which a privacy and performance characteristics of an ORAM can be configured ("tuned").

Cloud storage and computing are important tools to outsource data but have given rise to significant privacy concerns due to the non-local nature of data storage. Though encryption goes a long way in assuring data confidentiality, recent work [IKK14, DJR13] has shown that encryption is not sufficient. Encryption does not hide memory access patterns; an untrusted storage server can thus perform traffic analysis of memory access patterns to compromise client privacy. The work of Islam et al. has shown the leakage of sensitive keyword information by performing traffic analysis of access patterns over encrypted email [IKK14]. Similarly, Dautrich et al. have shown that access patterns over database tuples can leak ordering information [DJR13].

Oblivious RAM (ORAM), first introduced by Goldreich and Ostrovsky [GO96, Gol87], is a cryptographic primitive which allows a client to protect its data access pattern from an untrusted server storing the data. Since its introduction, substantial progress has been made by the research community in developing novel and efficient ORAM schemes [SVDS+13, RFK+b, GGH+13, DSS12, SSS11, RFK+a, SS13]. Recent work has also shown the promise of using ORAMs as a critical component in developing protocols for cryptographic primitives such as Secure Multi-Party Computation [GGH+13].

However, ORAM schemes can incur a large overhead in terms of bandwidth that renders them impractical. For example, even the most efficient ORAM protocols [SVDS+ 13, SSS11, RFK+b] incur a logarithmic overhead compared to conventional RAMs (e.g., greater than 100 times increase in communication including constants). This significantly impacts the throughput and latency of memory accesses, and presents a bottleneck for real-world deployment of ORAMs in high-performance and bandwidth constrained applications. The lack of low-bandwidth ORAMs, despite considerable efforts from the security community, is an undeniable indicator for the need of a new approach.

SUMMARY

In a general aspect, an approach to implementing or configuring an Oblivious RAM (ORAM) provides a way for the ORAM to meet a specified degree of privacy in a manner that avoids applying unnecessary computation resources (computation time, communication bandwidth and latency, and/or storages sizes) to achieve the specified degree of privacy. In this way, a tradeoff between privacy and computation resources may be tuned to address requirements of a particular application. This ability to tune this tradeoff is not found in other ORAM implementations, which in general aim to achieve complete privacy. In some implementations, the ORAM provides a constant bandwidth overhead compared to conventional RAMs, while achieving a statistical privacy guarantee.

In some examples, the general notion of differential privacy was developed by Dwork et al. [Dwo06] with its $(\epsilon,\delta)$-differential privacy modification [DKM+06]. In some examples, observable access patterns of the ORAM are computationally indistinguishable for different underlying RAM access. In a differentially private ORAM, the effect of a small change in RAM access pattern is characterized as a change in the probability distribution of the observable access pattern.

In one aspect, in general, a particular protocol family, referred to as "Root ORAM," provides tunable ORAM protocols allowing variable bandwidth overheads, system privacy and outsourcing ratios and including a design point that supports constant bandwidth construction and provide rigorous privacy guarantees of differentially private ORAMs. The low bandwidth protocols, achieved at the cost of statistical privacy and lower outsourcing ratios, are an order of magnitude improvement over previous work in which the protocols still incur a logarithmic bandwidth.

Aspects can include one or more of three features that are mutually compatible:
1. Use of a non-binary tree structure for access of storage units;
2. Migrating data blocks among storage buckets according to non-uniform probability distributions; and
3. Introduction of "fake" data accesses that do not implement read or write operations, yet nevertheless improve overall operation of the system.

The first two features generally reduce computation requirement at the expense of at least theoretically "leaking" information about the access pattern to an adversary. However, in practice, the amount of this information is negligible and not practically usable by an adversary. The third feature may increase communication requirements with the benefit of reducing private storage requirements in a domain that is not accessible to an adversary.

In one aspect, in general, a method provides private access to a memory system, which includes a plurality of addressable storage units (e.g., "buckets"). A first series of requests are received from a processor. Each request specifies an address of a memory block and an operation. The operations of the first series of requests include read operations and write operations. Each request specifying a write operation further specifies data to write at the specified address. A second series of requests to the memory system are determined from the first series of requests. The second series of requests implements the first series of requests by accesses to addressable storage units of the memory system. Each address specified in the requests of the first series of requests corresponds to a subset of the storage units of a plurality of N subsets of the storage units. Each subset has fewer than $1+\log_2 N$ storage units. Each subset has at least one storage units in common with every other subsets of the plurality of subsets. The second series of requests provide a degree of privacy of the addresses of the first series of requests. The second series of requests are caused to be performed by the memory system. For each request specifying an address of at least some of the requests of the first series of request corresponds to requests of the second series of requests, the method includes retrieving data from a current subset of storage units of the memory system associated with the address according to the maintained association, updating the subset of storage units associated with the address according to a non-uniform random selection from the plurality of N subsets, modifying the data of the retrieved subset of storage units according to the updated association of the address and the subsets, and providing the modified data for the current subset of storage units of the memory system.

Aspects may include one or more of the following features.

At least some of the requests of the second series of requests correspond to additional ("fake") requests that do not directly correspond to requests of the first series of requests.

The method further includes generating the additional requests according to a rate, $\lambda$, of requests of the first series per additional request.

Each subset of the plurality of subsets of storage units corresponds to a path in a tree with N leaf nodes from a root node to a leaf node of tree, each path having $\log_2 N$ or fewer nodes.

The tree comprises a K-level binary tree, for $K<\log_2 N$, and greater than two leaves of the tree at a K level are associated with each node of the binary tree.

In updating the subset of storage units associated with the address according to a non-uniform random selection from the plurality of N subsets, the non-uniform selection is according to probability distribution in which a probability $(1-p)$ of the updated subset being the same the current subset is greater than $1/N$.

The probability distribution is uniform with a probability $p/(N-1)$ for all subsets not being the same as the current subset.

Each storage unit is configured to store up to $Z>1$ encrypted memory blocks in association with their corresponding addresses.

Causing the second series of requests to be performed by the memory system comprises transmitting the second series of requests to the memory system.

Transmitting the second series of requests comprises transmitting said requests over a data network.

Transmitting the second series of requests comprises transmitting over a data bus on an integrated circuit.

In another aspect, in general, a memory interface implements all the steps of any one of the methods set forth above.

In another aspect, in general, a computer-readable medium has instructions stored thereupon, wherein execution of the instructions causes a data processing system to perform operations including all the steps of any one of the methods set forth above.

In another aspect, in general, a method provides private access to a memory system, which includes a plurality of addressable storage units. The method includes setting operational parameters of a memory interface according to specified degree of statistical privacy of memory access patterns, the operational parameters including a parameter of a non-uniform probability distribution for migration of data in the memory system, and a parameter specifying a rate of extra memory accesses; receiving a first series of requests from a processor, each request specifying an address of a memory block and an operation, the operations of the first series of requests including read operations and write operations, each request specifying a write operation further specify data to write at the specified address; and determining a second series of requests to the memory system from the first series of requests according to the operational parameters, execution of the first series of requests being implemented using execution of the second series of requests, the second series of requests maintaining the specified degree of statistical privacy of memory access patterns, without maintaining complete privacy of said memory access patterns.

A differentially private ORAM approach in which the parameters of an ORAM are selected to achieve a specified degree of privacy provides a solution to the technological problem of data access privacy without using excessive computation resources. Therefore, when only a certain degree of privacy is required, the approach improves the functioning of a computing system by reducing the amount of communication between a processor and a memory system, or the amount of storage local to the processor as compared to presently available approaches.

DETAILED DESCRIPTION

Figure 1:
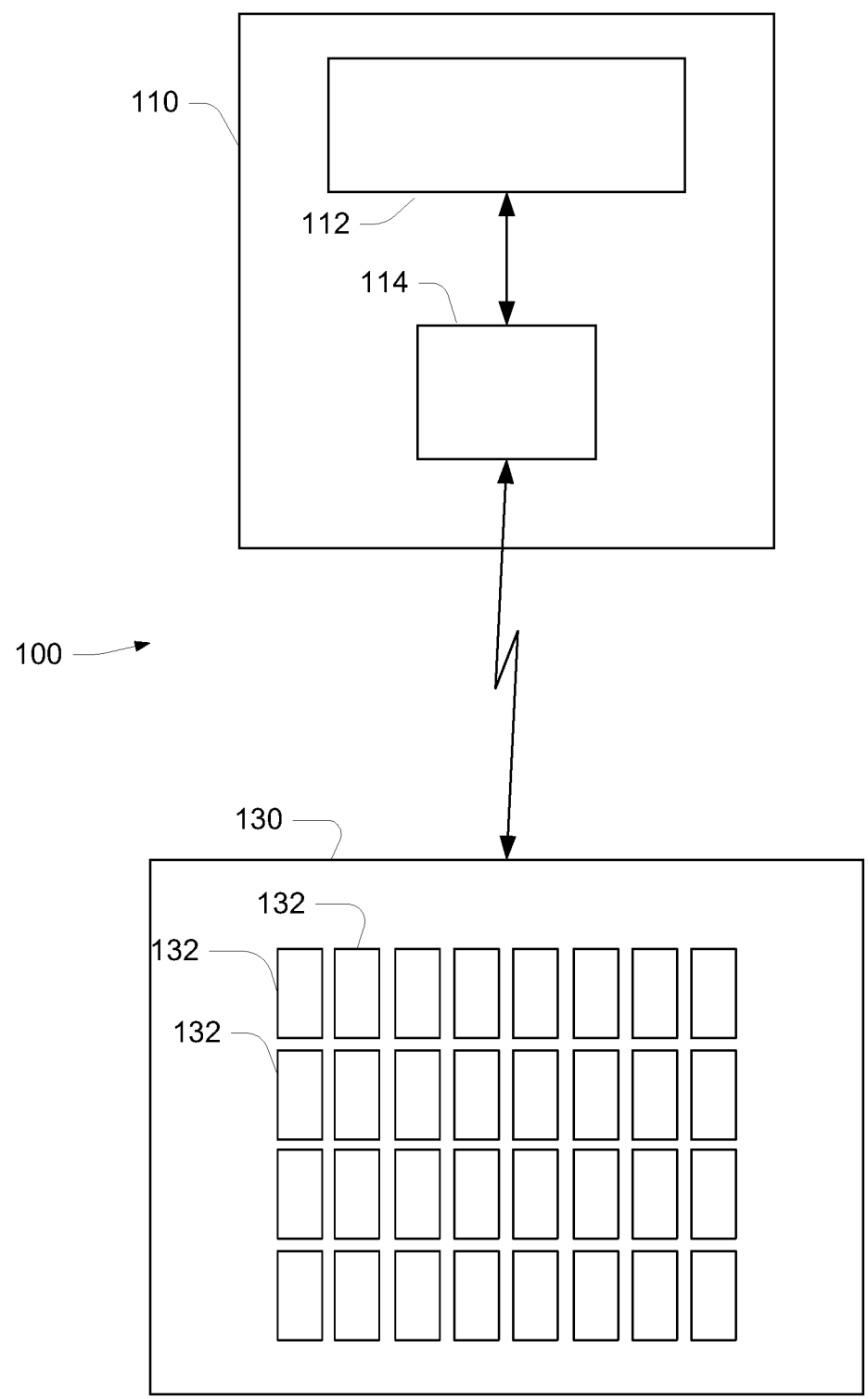
FIG. 1 is a block diagram of a computation system with an ORAM.

Referring to FIG. 1, a data processing system 100 has a computation system 110, a memory system 130, and a communication link 120 between the computation system 110 and the memory system 130. The computation system 110 is assumed to be a secure domain in that adverse parties are prevented from accessing data within the computation system or view the internal operation of the computation system. For example, encrypted data may be delivered from the memory system 130 over the communication link 120 to the computation system 110. Internal to the computation system, the encrypted data is decrypted. Therefore an adversary that observes the encrypted data traversing the link 120, or that has access to the encrypted data in the memory system 130, is prevented from accessing the data because of the encryption. However, the adversary can observe the access pattern over the link 120. It should be recognized that the access pattern itself may expose information to an adversary. As an example, the communication link is a computer bus or a data network, and the memory system is a block-based disk or semiconductor storage system. As a more specific example, the computation system 110 is in a personal computer, which accesses a block-based storage service, for example, the Amazon EC2 system, over the public Internet.

The storage system 130 has a set of addressable "buckets" 132, the computing system 110 may send read or write requests over the communication link 120. As introduced above, the data transmitted with or received in response to these requests is encrypted with keys that are within the secure domain of the computing system 110.

Internal to the computation system 110 is a processor 112. The processor emits memory a sequence of requests $y_1$, $y_2$, ..., $y_n$ for read or write operations on addressable blocks. The size of these addressable blocks is smaller than the size of the buckets 132 of the storage system. In the discussion below, each bucket can store data form Z addressable blocks. A processor request can be represented as a triple $y_i=(op_i, a_i, d_i)$ where $op_i$ is either "read" or "write", $a_i$ is the address of the block to be read or written, and in the case of a write, $d_i$ is the data to be written to the addressed block. In the case of a read operation, the retrieved data in a block is returned to the processor 112. In some implementations, a "remove" operator can be implemented using a write operation where the data written is a randomized encryption of 0 (i.e., an empty (a, d) segment). Not shown in FIG. 1 is the structure of the processor, including a central processing unit (CPU), which executes instructions including memory instructions that in general address smaller units of memory. For example, the size of each bucket of the memory system 110 may be 10240 bytes, while the CPU may make memory requests for blocks of 1024 bytes per request (i.e., Z=10).

Overview

As introduced above, a bucket 132 of the memory system 130 contains Z segments, each of which can store a randomly encrypted data block in association with its address, (a, d), or be empty but filled with dummy data and randomly encrypted so that is does not appear different than used segments. By random encryption, we mean that when the same data is repeatedly encrypted, there is additional randomness so that the same encrypted form is not repeated. A data block can potentially resides in any bucket of the memory system. Over time, a particular block (a, d) migrates between buckets, residing in only a single bucket at a time. A bucket is the smallest unit that is transferred over the communication link 120. Continuing to refer to 1, the computation system 110 includes an ORAM interface 114, which receives requests $y_i$ from the processor 112, and emits bucket-oriented read and write requests to the memory system 130. The ORAM interface performs the requisite encryption and decryption, and as described below maintains organization data that permits it to map a requested to access a block at an address a to multiple requests to access buckets corresponding to the address. As is described further below, to access each block, rather than merely accessing a single bucket in which an addressed block is stored, the ORAM interface accesses a larger set of buckets in a manner that makes it impossible or difficult for an adversary to determine what address a is being accessed.

Figure 2:
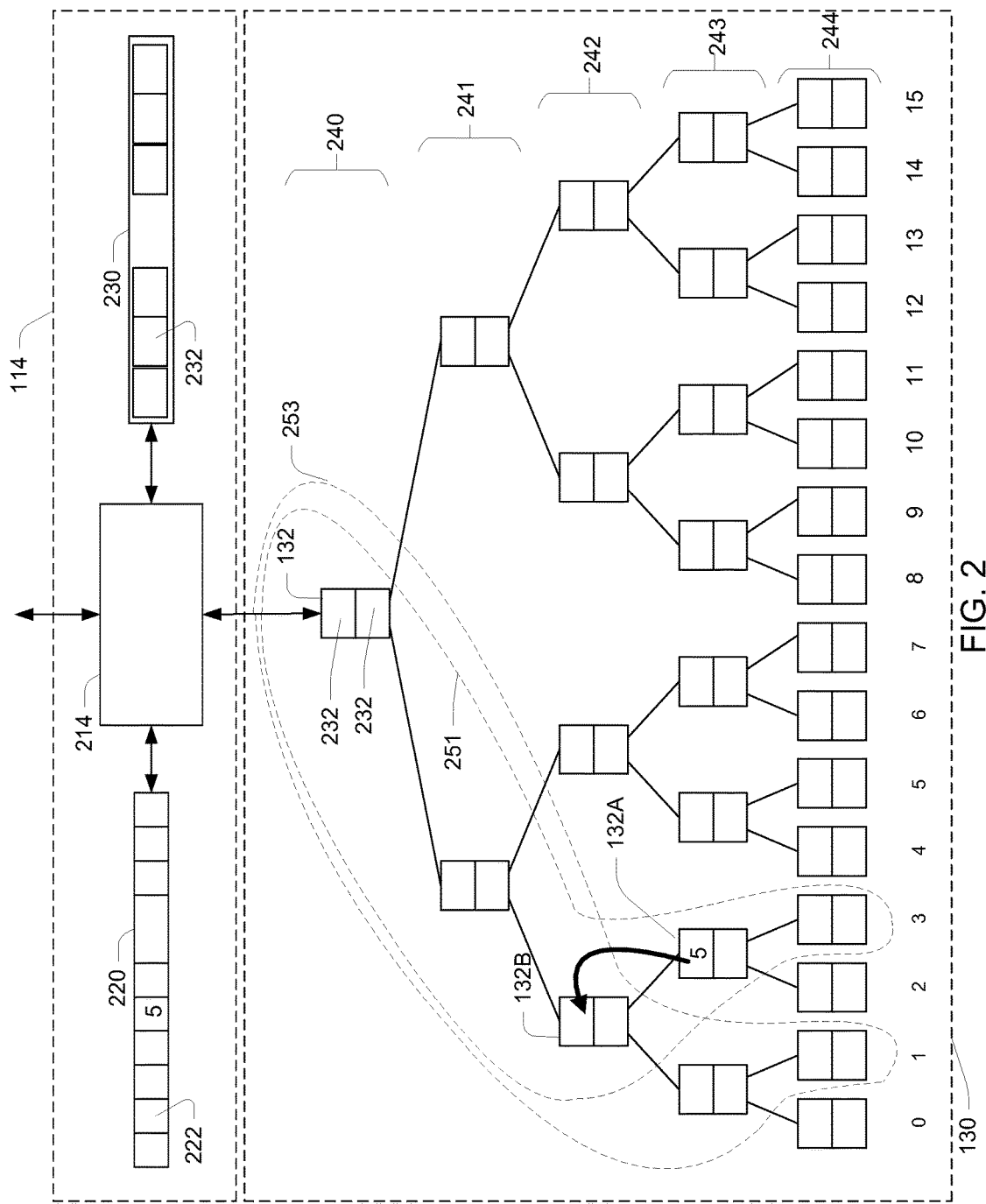
FIG. 2 is a block diagram of a binary tree based ORAM.

Referring to FIG. 2, in some implementations, the buckets 132 of the storage system 130 are arranged (at least from the point of view of the computation system 110) in a binary tree structure. In this example, there are $N=2^L=16$ leaves, for a total of 32 buckets 132, arranged in L+1 levels 240-244, indexed k=0, ..., L. The leaf nodes are index from x=0 to x=N−1. In general, the number of leaves is equal to the number of addressable blocks, but this feature is not required. The buckets in a path from the root node of the tree to a leaf x are denoted P(x), and the bucket at level i is denoted by P(x, i), where the root of the tree is at level i=0. For example, the buckets of P(3) are illustrated as a group 253, and the buckets P(1) are illustrated as a group 251.

The ORAM interface 114 includes a protocol controller 214, as well as a positional storage 220, which stores a positional mapping x=pos[a] from addresses a to leaves x. That is, each address that is requested by the processor 112 has an entry 222 in the positional storage. In the figure, the block with address a=5 is illustrated as being associated with the leaf with index 5. A block itself is not necessarily stored in the bucket at the leaf to which the block is assigned. Rather, the block is stored in one of the buckets in the path to that leaf. In the illustration, the block with address a=5 is stored in a bucket 132A at level k=3.

In general, a request to read a block at address a is mapped by the ORAM protocol controller 214 into a set of requests to read all the buckets on the path P(pos[a]). The controller 214 receives all the encrypted buckets, decrypts them, and extracts the requested data block and passes that data back to the processor 112.

Following the read of all the buckets on the path, controller 214 writes back to the same set of buckets in the storage system. Prior to the writing back the buckets, the ORAM interface updates the mapping of the read block a to a new pos[a] with a random assignment. In the example illustrated in FIG. 2, the address a=5 is mapped to a new leaf with index 1. With the new assignment, the block cannot be written back to the same bucket 132A, because it does not belong to the new path P(1) illustrated as group 251 in the figure. Rather, the block for a=5 must now be written to a bucket that is both in path P(1) and P(3), because it is the buckets of P(3) that are going to be written back. For example, block a=5 is written to a bucket 132B, which is both in P(3) and P(1) In addition to moving the read block, the controller 214 moves certain of the blocks from one bucket to another, generally toward the leaf buckets, maintaining the requirement that they remain in the paths according to their assigned positions.

Note that it is possible that as a result of the update of the position of read address, there is no room to store the data in a suitable bucket. In such a situation, the block is stored locally in the ORAM interface 114 in a memory area referred to as the "stash" 230. The stash includes a number of segments 232, each for storing data for a block in association with its address. Note also that in the block moving procedure, if possible, data blocks in the stash are moved to buckets before the write back to the memory system.

It should be recognized because the data for a block associated with a leaf may reside in any bucket on the path to that leaf, an interior (non-leaf) bucket may have data blocks associated with any leaf of the subtree rooted at that bucket. Subject to availability of unused segments in the buckets to be written back, the blocks are moved as far as possible to buckets nearest to (or at the leaf of the path) without violating the requirement that a block's assigned leaf is in the subtree below node of the bucket in which it is stored.

In general, a request to write a block at address a is first mapped by the ORAM interface to a set of requests to read all the buckets on the path P(pos[a]). The ORAM interface receives all the encrypted buckets and decrypts them. After performing the update of pos[a], and the migration procedure on the blocks described above, the updated block is either stored in the stash or in a suitable bucket before the buckets are written back.

Note that in the case that the updated positions are chosen uniformly at random over all the leaves, an adversary cannot determine a pattern of access to the underlying addresses. The overhead of the approach described above is that the reading or writing of one block results in reading and writing of K+1 buckets, where K+1 is the depth of the tree, with each bucket including Z blocks. Therefore, for a binary tree with $N=2^K$ levels, the communication overhead is O(Z log N), and the local storage overhead is O(Z)

Non-Binary Tree

Figure 3:
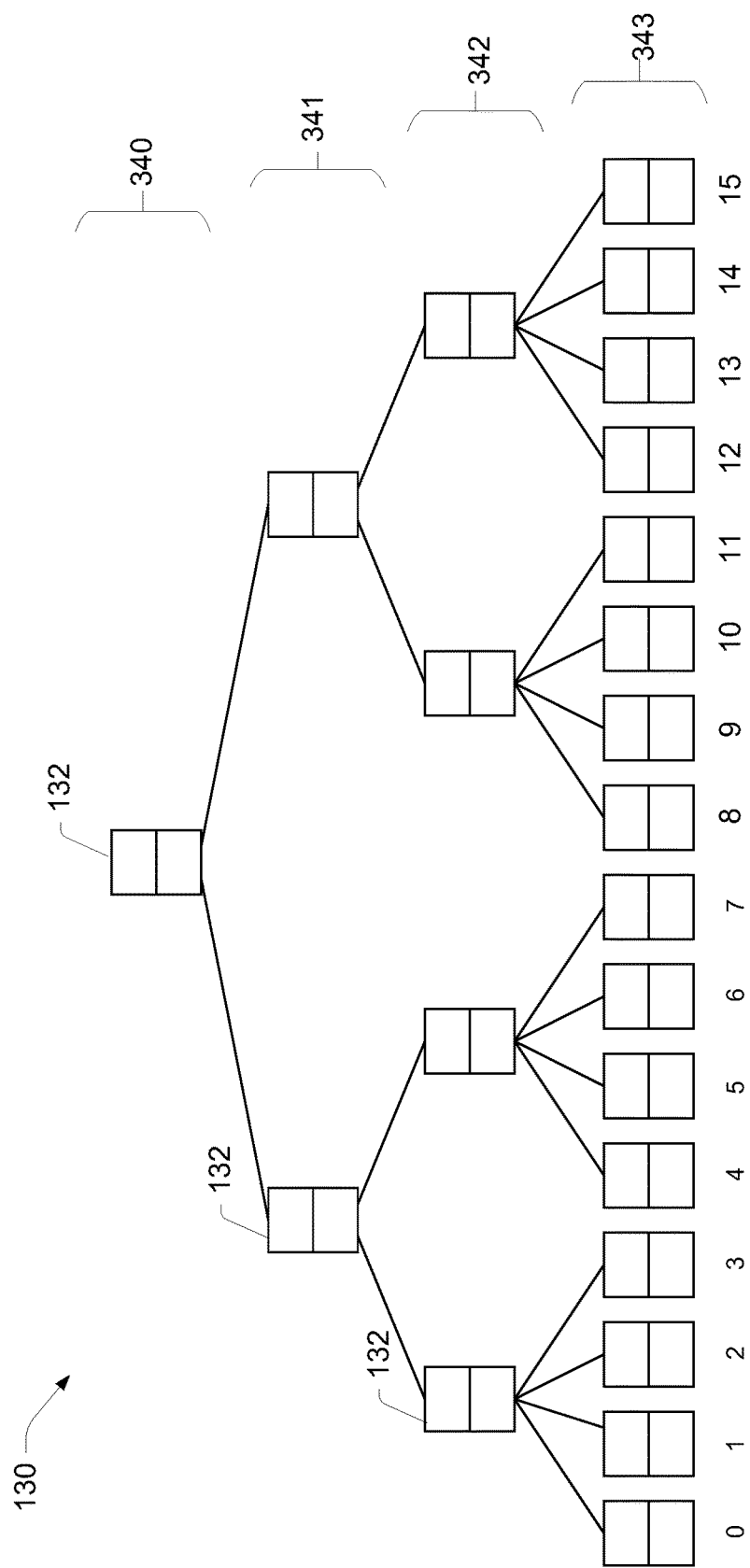
FIG. 3 is a non-binary tree ORAM storage.

Referring to FIG. 3 as an alternative to the binary tree arrangement of buckets 132 in a storage system 132 shown in FIG. 2, a non-binary tree structure may be used. In general, a tree structure with K+1 levels such that K<L=$\log_2$ N is chosen. In the example illustrated in FIG. 3, with N=16 only K+1=4 levels are used. As a result, K+1 buckets are read and then written for each processor access. The smaller K is, the lower the communication overhead. In the example shown in FIG. 3, the first K=3 levels form a binary tree, and each for the nodes of that binary tree has $2^{L-K+1}$ children, in this case 4 children. Other than the change in the structure of the tree, operation proceeds in the same manner as described above.

However, it should be recognized that a consequence of reducing K is that there may be fewer opportunities to move blocks from the stash to the memory system, or the move a written block back to the storage system rather than to the stash. With high probability, the stash will not exceed much beyond the expected value. A practice, a solution to avoid stash overflow is to perform fake accesses until sufficient space is freed in the stash.

Non-Uniform Migration

As described above, on each read or write access to a block, the controller 214 randomly assigns a new position for the referenced block. In the example discussed with reference to FIG. 2, a block at address a=5 is migrated from leaf x=3 to a leaf x=1 and relocate from a bucket 132A to a bucket 132B. In the case of a binary tree, the probability that the old and the new paths will only intersect at level k=0 is ½, that they will intersect exactly two levels is ¼ and so forth. But because the segments of the buckets at those level may be full and the data in the segments of the bucket may not be movable to lower levels before the write of the path, there is at least some probability that a written segment may have to be stored in the stash.

As an alternative to choosing the new leaf for an address from a distribution Pr(x)=1/N over the N leaves, a non-uniform distribution is used. As one example, for a prior assigned leaf $x_0$, probability of the next leaf is set to $$Pr(x \mid x_0) = \begin{cases} 1-p & \text{if } x = x_0 \\ p/(N-1) & \text{otherwise} \end{cases}$$

It should be understood that other non-uniform distributions can be used, with each such distribution inducing a desired distribution of how many nodes in the tree overlap between the path $P(x_0)$ and a new path $P(x_1)$ where $x_1$ is drawn from the distribution $Pr(x \mid x_0)$.

A consequence of there being a greater number of overlapping buckets, on average, is that more blocks may be moved between buckets closer to the leaves on each write of a path to the memory system, and more blocks may be moved from the stash to the memory system on each such write, again on average. A privacy consequence is that there may be some information that "leaks" related to the migration of blocks from bucket to bucket. However, there in general, it is not clear that there is any efficient means for an adversary to use this information to infer the underlying block access pattern.

In combination with a reduced depth non-binary tree, which may reduce the movement of blocks toward the leaves and increase the required size of the stash 230, the use of a non-uniform migration distribution increases the movement to the leaves and from the stash. Therefore these two features have some offsetting effects. For example, the parameters K and p may be optimized to yield a desired computation (storage and communication) load and a corresponding level of privacy.

Fake Accesses

Another aspect of a number of embodiments makes use of "fake" accesses. The general idea is that in addition to real read or write requests for blocks by the processor 112, the ORAM interface 114 autonomously generates "fake" requests, which are indistinguishable to an adversary on the communication path 120 or in the memory system 130 from real requests.

Assuming that there is at least one block in the stash 230, the ORAM controller 214 from time to time makes a random selection of a (a, d) element of the stash. It then essentially follows the procedure to write that block once again. As described above, this involves reading the path of buckets for the current position of a, updating the position of a, migrating blocks within the buckets of the path, and if possible from the stash to the path, and writing back the blocks of the path. If the stash is empty, a random leaf may be selected, or a fake access is not necessarily performed.

In general, the effect of the fake access is to move blocks toward the leaves of the tree, and to clear blocks from the stash to the memory system, at least statistically (i.e., there may be fake accesses that don't result in these effects, but on average they do).

An approach to insertion of fake accesses is to, on average, insert one fake access per A, real accesses. One way of accomplishing this is to draw a random value a from a Poisson distribution with parameter λ, and present a run of a real accesses followed by one fake access. Because the expected value of α is λ, the long term average rate of fake accesses is achieved. Other approaches may be used as well, for example, introducing a fake access after every real access with a probability 1/λ.

In some implementations, a fake access uses a current position of a block and performs the procedure for a write of that block. Alternatively, a block in the stash is first randomly migrated to a new position, and then the new path is read and then written, generally resulting in at least the migrated block being written pack to the ORAM storage.

In combination with a reduced depth non-binary tree, which may reduce the movement of blocks toward the leaves and increase the required size of the stash 230, fake accesses increases the movement to the leaves and from the stash. Therefore these two features have some offsetting effects. For example, the parameters K and λ may be optimized to yield a desired computation (storage and communication) load and a corresponding level of privacy. Furthermore, with a reduced depth non-binary tree, the combination of non-uniform migration distribution and fake accesses together increase the movement to the leaves and from the stash. Therefore these features have offsetting effects. For example, the three parameters K, p, and λ may be optimized to yield a desired computation load and a corresponding level of privacy.

Differential Privacy

The notion of statistical privacy, which may have been used in other applications, is adapted to characterize the privacy of the ORAM approach described above. Formally, the ORAM approach described above provide a mechanism (which is randomize randomized), which takes an input access sequence $\vec{y}$ as given below, $$\vec{y} = ((op_M, addr_M, data_M), \ldots, (op_1, addr_1, data_1)) \quad (1)$$

and outputs a resulting output sequence denoted by ORAM($\vec{y}$). Here, M is the length of the access sequence, $op_i$ denotes whether the $i^{th}$ operation is a read or a write, $addr_i$ denotes the address for that access, and $data_i$ denotes the data (if $op_i$ is a write). Denoting by $|\vec{y}|$ the length of the access sequence $\vec{y}$, the currently accepted privacy definition for ORAM privacy can be summarized as follows [SVDS+13]:

Let $\vec{y}$ as given in Eq. 1, denote an input access sequence. Let ORAM($\vec{y}$) be the resulting randomized data request sequence of an ORAM algorithm. The ORAM protocol guarantees that for any $\vec{y}$ and $\vec{y}'$, ORAM($\vec{y}$) and ORAM($\vec{y}'$) are computationally indistinguishable if $|\vec{y}|=|\vec{y}'|$, and also that for any $\vec{y}$ the data returned to the client by ORAM is consistent with $\vec{y}$ (i.e the ORAM behaves like a valid RAM) with high probability.

Instead of using a complete privacy approach, the following statistical notion of an ORAM is used. The intuition behind a differentially private ORAM is that given any two input sequences that differ in a single access, the distributions of their output sequences should be "close." In other words, similar access sequences lead to similar distributions. Hence an adversary observing a sample from either distribution cannot distinguish well with good accuracy. We formally define it as follows:

Let $\vec{y}$, as defined in Eq. 1, denote the input to an ORAM. Let ORAM($\vec{y}$) be the resulting randomized data request sequence of an ORAM algorithm. We say that a ORAM protocol is ($\epsilon,\delta$)-differentially private if for all input access sequences $\vec{y}_1$ and $\vec{y}_2$, which differ in at most one access, the following condition is satisfied by the ORAM protocol, $$Pr[ORAM(\vec{y}_1) \in S] \le e^{\epsilon} Pr[ORAM(\vec{y}_2) \in S] + \delta \qquad (2)$$

where S is any set of output sequences of the ORAM.

Note that the formalism does not make any assumption about the size of the output sequences in S. Thus, if the input to the ORAM is changed by a single access tuple ($op_i$, $addr_i$, $data_i$), the output distribution does not change significantly. It is important to note that the differential privacy guarantees when two access patterns differ in multiple elements directly follows from the composability property of differential privacy. Since this property is extremely important for the utility of the mechanism, we summarize this in the form of a theorem:

Given two access sequences $s_1$ and $s_2$ that differ in m accesses, a ($\epsilon,\delta$)-differentially private ORAM mechanism guarantees, $$Pr[ORAM(s_1) \in S] \le e^{m\epsilon} Pr[ORAM(s_2) \in S] + m\delta \qquad (3)$$

The proof of the theorem directly follows from the composability property of the differential privacy mechanism [?]. In other words, the present ORAM approach guarantees can be extended to sequences which differ in multiple accesses and hence can be used to give rigorous guarantees for arbitrary access sequences.

Tuning

In a configuration that uses all three of the features described above, including a reduced depth tree according to a parameter K, a non-uniform migration distribution with a single parameter, p (i.e., repeating the same path with probability 1−p), and a fake access insertion rate of one fake access per λ real accesses, these parameters may be selected based a characterization of the privacy of the resulting system.

Given a stash size C, the ORAM approach with configuration parameters K, p, Z and λ is ($\epsilon,\delta$)-differentially private for $$\epsilon = 2\log\left(\frac{(N-1)(1-p)}{p}\right)$$

and $$\delta = (1-p)^{M_K}$$

where $M_K = (C+Z(K+1)+1)$. Therefore, given values of $\epsilon$ and $\delta$, suitable configuration parameters may be found to satisfy the above equations. Due to a conservative privacy analysis, λ does not appear in the above expressions, and as λ is reduced, the privacy increases beyond the ($\epsilon,\delta$) level specified by the expressions.

Given an ORAM scheme with an unbounded amount of local stash, it can be shown that such a scheme is $\epsilon$-differentially private. But with a finite amount of stash, this is no longer true and the privacy loss under such a situation is the quantity that is bounded by $\delta$. In the context of the present ORAM approach, $\delta$ quantifies the privacy loss if the stash size is exceeded.

The bandwidth of the ORAM approach with configuration parameters K, p, Z and λ is $$2 \times Z(k+1) \times (1+1/\lambda)$$

per real access.

Recursion

In some implementations, the storage of the positional storage 220 and/or the stash 230 uses a second ORAM in a recursive manner. Note that this storage requires O(N) storage capacity. In a basic manner, recursion can be used a follows. The position map on the server as a secondary ORAM, say $ORAM_2$. Now the blocks of this second ORAM contain the position map values. Since they just require log N bits to store, we can store a number of them in each block (say at least 2). Hence, our secondary ORAM, $ORAM_2$ is not of a small size and hence the position map for this one is smaller (at most half of the original size (which is N)). Continuing this recursively a few times, the overhead of storing the position map locally is reduced. If done log N number of times, the storage overhead is a constant size. From a usage point of view, the ORAM's are queried in the reverse order, i.e., taking the smallest ORAM, its position map is stored locally and look up the path to read and write in the next ORAM. Retrieve that block and it will contain the information to the which path needs to be read in the next ORAM and so on. The number of levels of recursion can be modified to suit the users' needs. Similarly, the size of the blocks of each individual ORAM can be modified and in particular, can be different form the block size of the main ORAM (which stores real user data).

Implementation

The approaches described above may be implemented in software, in hardware, or in a combination of software and hardware. The software may include instructions stored on a non-transitory machine-readable medium for causing a processor to before the steps of the methods described above. The processor may be a physical processor, a virtual processor, or an interpreter. Hardware may include Application Specific Integrated Circuits (ASICs), or Field Programmable Gate Arrays (FPGAs). In some examples, the computation system 110 is a secure processor (or a secure region of an integrated circuit) with the ORAM interface being implemented in hardware, and the communication link 120 is a bus to a local memory system (e.g., dynamic RAM). In another example, the computation system 110 is a personal computer or other physically secure computer, with the ORAM interface being implemented in software, and the communication path 120 is over a data network accessible to an adversary. In some examples, the storage system 130 is a "cloud" based storage system (e.g., Amazon EC2), the stored data in the system being potentially accessible to an adversary.

Alternatives

The parameters p and λ can be changed on-the-fly and the corresponding privacy properties remain. Such adaptation or changing of parameters does not need any additional infrastructural changes to change them on-the-fly (unlike the number of blocks N, which may be more difficult to change adaptively.)

Other arrangements of buckets than trees in which overlapping subsets may be used rather than tree-based paths. Although certain aspects of performance may be improved over use of the tree structures described above, certain formal results guaranteeing the (ε,δ) statistical privacy are not presently proved for such other structures. Similarly, the size of the tree and/or the number of paths does not have to be equal to the number of blocks that can be stored in the ORAM (e.g., there may be a smaller number or a greater number of blocks). However, the formal privacy guarantees for such alternatives are not necessarily presently available for such alternatives.

It is to be understood that the foregoing description is intended to illustrate and not to limit the scope of the invention, which is defined by the scope of the appended claims. Other embodiments are within the scope of the following claims.

REFERENCES

[DJR13] Jonathan L Dautrich Jr and Chinya V Ravishankar. Compromising privacy in precise query protocols. In *Proceedings of the 16th International Conference on Extending Database Technology*, pages 155-166. ACM, 2013.

[DKM+06] Cynthia Dwork, Krishnaram Kenthapadi, Frank McSherry, Ilya Mironov, and Moni Naor. Our data, ourselves: Privacy via distributed noise generation. In *Advances in Cryptology-EUROCRYPT* 2006, pages 486-503. Springer, 2006.

[DSS12] Jonathan Dautrich, Emil Stefanov, and Elaine Shi. Burst oram: Minimizing oram response times for bursty access patterns. In *USENIX Security*, 2012.

[Dwo06] Cynthia Dwork. Differential privacy. In *Automata, languages and programming*, pages 1-12. Springer, 2006.

[GGH+13] Craig Gentry, Kenny A Goldman, Shai Halevi, Charanjit Julta, Mariana Raykova, and Daniel Wichs. Optimizing oram and using it efficiently for secure computation. In *Privacy Enhancing Technologies*, pages 1-18. Springer, 2013.

[GO96] Oded Goldreich and Rafail Ostrovsky. Software protection and simulation on oblivious rams. *Journal of the ACM (JACM)*, 43(3):431-473, 1996.

[Gol87] O. Goldreich. Towards a theory of software protection and simulation by oblivious rams. In *Proceedings of the Nineteenth Annual ACM Symposium on Theory of Computing*, STOC '87, pages 182-194, New York, N.Y., USA, 1987. ACM.

[IKK14] MS Islam, Mehmet Kuzu, and Murat Kantarcioglu. Access pattern disclosure on searchable encryption: Ramification, attack and mitigation. In *Proc. NDSS*, volume 14, 2014.

[RFK+a] Ling Ren, Christopher W Fletcher, Albert Kwon, Emil Stefanov, Elaine Shi, Marten van Dijk, and Srinivas Devadas. Constants count: Practical improvements to oblivious ram. In *24th USENIX Security Symposium (USENIX Security* 15). USENIX Association.

[RFK+b] Ling Ren, Christopher W Fletcher, Albert Kwon, Emil Stefanov, Elaine Shi, Marten van Dijk, and Srinivas Devadas. Ring oram: Closing the gap between small and large client storage oblivious ram. Technical report, Cryptology ePrint Archive, Report 2014/997, 2014. http://eprint.iacr.org.

[SS13] Emil Stefanov and Elaine Shi. Oblivistore: High performance oblivious cloud storage. In *Security and Privacy (SP)*, 2013 *IEEE Symposium on*, pages 253-267. IEEE, 2013.

[SSS11] Emil Stefanov, Elaine Shi, and Dawn Song. Towards practical oblivious ram. *arXiv preprint arXiv:1106.3652*, 2011.

[SVDS+13] Emil Stefanov, Marten Van Dijk, Elaine Shi, Christopher Fletcher, Ling Ren, Xiangyao Yu, and Srinivas Devadas. Path oram: An extremely simple oblivious ram protocol. In *Proceedings of the* 2013 *ACM SIGSAC conference on Computer & communications security*, pages 299-310. ACM, 2013.

What is claimed is:

1. A method for private access to a memory system, the memory system including plurality of addressable storage units, the method comprising:

receiving a first series of requests from a processor, each request specifying an address of a memory block and an operation, the operations of the first series of requests including read operations and write operations, each request specifying a write operation further specifying data to write at the specified address;

determining a second series of requests to the memory system from the first series of requests from the processor, wherein the second series of requests implements the first series of requests by accesses to addressable storage units of the memory system, each address specified in the requests of the first series of requests corresponding to a subset of the storage units of a plurality of N subsets of the storage units, each subset having fewer than $1+\log_2 N$ storage units, each subset having at least one storage units in common with every other subset of the plurality of subsets, and the second series of requests provide a degree of privacy of the addresses of the first series of requests; and causing the second series of requests to be performed by the memory system;

wherein for each request specifying an address of at least some of the requests of the first series of request corresponds to requests of the second series of requests, the method includes retrieving data from a current subset of storage units of the memory system associated with the address according to a maintained association of addresses and storage units, updating the maintained association by updating the subset of storage units associated with the address according to a non-uniform random selection from the plurality of N subsets, modifying the data of the retrieved subset of storage units according to the updated association of the address and the subsets, and providing the modified data for the current subset of storage units of the memory system.

2. The method of claim 1 wherein at least some of the requests of the second series of requests correspond to additional requests that do not directly correspond to requests of the first series of requests.

3. The method of claim 2 further comprising generating the additional requests according to a rate, $\lambda$, of requests of the first series per additional request.

4. The method of claim 1 wherein each subset of the plurality of subsets of storage units corresponds to a path in a tree with N leaf nodes from a root node to a leaf node of tree, each path having $\log_2 N$ or fewer nodes.

5. The method of claim 4 wherein the tree comprises a K-level binary tree, for $K<\log_2 N$, and a further level with a fanout greater than two.

6. The method of claim 1 wherein in updating the subset of storage units associated with the address according to a non-uniform random selection from the plurality of N subsets, the non-uniform random selection is according to probability distribution in which a probability $(1-p)$ of the updated subset being the same the current subset is greater than $1/N$.

7. The method of claim 6 wherein the probability distribution is uniform with a probability $p/(N-1)$ for all subsets not being the same as the current subset.

8. The method of claim 1 wherein each storage unit is configured to store up to a number $Z>1$ encrypted memory blocks in association with their corresponding addresses.

9. The method of claim 1 wherein causing the second series of requests to be performed by the memory system comprises transmitting the second series of requests to the memory system.

10. The method of claim 9 wherein transmitting the second series of requests comprises transmitting said requests over a data network.

11. The method of claim 9 wherein transmitting the second series of requests comprises transmitting over a data bus on an integrated circuit.

12. A method for private access to a memory system, the memory system includes a plurality of addressable storage units, the method comprising:

setting operational parameters of a memory interface according to specified degree of statistical privacy of memory access patterns, the operational parameters including a parameter of a non-uniform probability distribution for migration of data in the memory system, and a parameter specifying a rate of extra memory accesses;

receiving a first series of requests from a processor, each request specifying an address of a memory block and an operation, the operations of the first series of requests including read operations and write operations, each request specifying a write operation further specify data to write at the specified address; and determining a second series of requests to the memory system from the first series of requests according to the operational parameters, execution of the first series of requests being implemented using execution of the second series of requests, the second series of requests maintaining the specified degree of statistical privacy of memory access patterns, without maintaining complete privacy of said memory access patterns.

13. A memory interface comprising:

a controller having a first interface for communicating with a processor for receiving requests from the processor and providing responses to the processor, each request specifying an address of a data block and an operation, the operations of the requests including read operations and write operations, and a second interface for accessing a plurality of addressable storage units of a memory system, each storage unit of the memory system providing a storage for a plurality of data blocks;

a positional storage for storing an association of addresses of data blocks and addressed of storage units of the memory system; and wherein the controller is configured to receive a first series of requests via the first interface, each request specifying an address of a memory block and an operation, the operations of the first series of requests including read operations and write operations, each request specifying a write operation further specifying data to write at the specified address, determine a second series of requests from the first series of requests for sending via the second interface, the second series of requests implementing the first series of requests by accesses to addressable storage units of the memory system, each address specified in the requests of the first series of requests corresponding to a subset of the storage units of a plurality of N subsets of the storage units, each subset having fewer than $1+\log_2 N$ storage units, each subset having at least one storage units in common with every other subsets of the plurality of subsets, the second series of requests providing a degree of privacy of the addresses of the first series of requests, and cause the second series of requests to be performed by the memory system; and wherein the controller is further configured to, for each request specifying an address of at least some of the requests of the first series of request corresponds to requests of the second series of requests, access the positional storage to determine a current subset of storage units of the memory system associated with the address according to the maintained association retrieve data from the current subset of storage units of the memory system, update the positional storage, including updating the subset of storage units associated with the address according to a non-uniform random selection from the plurality of N subsets, modify the data of the retrieved subset of storage units according to the updated association of the address and the subsets, and provide the modified data for the current subset of storage units of the memory system.

14. The controller of claim 13 further comprising a local block storage for data blocks, including data blocks for which the controller has received write operation requests and the data blocks have not been written to storage units of the memory system.

15. A computer-readable medium having instructions stored thereupon, wherein execution of the instructions causes a data processing system to provide private access to a memory system, the memory system includes a plurality of addressable storage units, the providing of the private access including:

receiving a first series of requests from a processor, each request specifying an address of a memory block and an operation, the operations of the first series of requests including read operations and write operations, each request specifying a write operation further specifying data to write at the specified address;

determining a second series of requests to the memory system from the first series of requests, the second series of requests implementing the first series of requests by accesses to addressable storage units of the memory system, each address specified in the requests of the first series of requests corresponding to a subset of the storage units of a plurality of N subsets of the storage units, each subset having fewer than $1+\log_2 N$ storage units, each subset having at least one storage units in common with every other subsets of the plurality of subsets, the second series of requests providing a degree of privacy of the addresses of the first series of requests; and causing the second series of requests to be performed by the memory system;

wherein for each request specifying an address of at least some of the requests of the first series of request corresponds to requests of the second series of requests, the method includes retrieving data from a current subset of storage units of the memory system associated with the address according to the maintained association, updating the subset of storage units associated with the address according to a non-uniform random selection from the plurality of N subsets, modifying the data of the retrieved subset of storage units according to the updated association of the address and the subsets, and providing the modified data for the current subset of storage units of the memory system.

\* \* \* \* \*